(12) United States Patent
Padmanabhan et al.

(10) Patent No.: US 8,361,410 B2
(45) Date of Patent: Jan. 29, 2013

(54) FLOW METERED ANALYZER

(75) Inventors: Aravind Padmanabhan, Plymouth, MN (US); Cleopatra Cabuz, Eden Prairie, MN (US)

(73) Assignee: Honeywell International Inc., Morristown, NJ (US)

( * ) Notice: Subject to any disclaimer, the term of this patent is extended or adjusted under 35 U.S.C. 154(b) by 1277 days.

(21) Appl. No.: 11/428,332

(22) Filed: Jun. 30, 2006

(65) Prior Publication Data

US 2007/0003434 A1 Jan. 4, 2007

Related U.S. Application Data

(60) Provisional application No. 60/696,162, filed on Jul. 1, 2005.

(51) Int. Cl.
*G01N 21/00* (2006.01)
(52) U.S. Cl. .......... 422/400; 422/502; 422/503
(58) Field of Classification Search .......... 422/400, 422/502, 503
See application file for complete search history.

(56) References Cited

U.S. PATENT DOCUMENTS

| | | | |
|---|---|---|---|
| 3,731,524 A | 5/1973 | Langley et al. |
| 3,822,095 A | 7/1974 | Hirschfeld |
| 3,928,094 A | 12/1975 | Angell |
| 3,976,862 A | 8/1976 | Curbelo |
| 4,284,412 A | 8/1981 | Hansen et al. |
| 4,478,076 A | 10/1984 | Bohrer |
| 4,478,077 A | 10/1984 | Bohrer et al. |
| 4,501,144 A | 2/1985 | Higashi et al. |
| 4,599,000 A | 7/1986 | Yamada |
| 4,651,564 A | 3/1987 | Johnson et al. |
| 4,664,056 A | 5/1987 | Jehanno |
| 4,683,159 A | 7/1987 | Bohrer et al. |
| 4,695,034 A | 9/1987 | Shimizu et al. |
| 4,704,033 A | 11/1987 | Fay et al. |
| 4,745,279 A | 5/1988 | Karkar et al. |
| 4,818,263 A | 4/1989 | Mitch |
| 4,874,949 A | 10/1989 | Harris et al. |
| 4,911,616 A | 3/1990 | Laumann, Jr. |
| 4,932,989 A | 6/1990 | Presby |
| 5,017,497 A | 5/1991 | Gerard de Grooth et al. |
| 5,050,429 A | 9/1991 | Nishimoto et al. |
| 5,078,581 A | 1/1992 | Blum et al. |

(Continued)

FOREIGN PATENT DOCUMENTS

| | | |
|---|---|---|
| DE | 3127560 | 2/1983 |
| DE | 10122321 | 4/2002 |

(Continued)

OTHER PUBLICATIONS http://www.micronics.net/tsensor.htm, pp. 1-4, downloaded Jun. 14, 2000.

(Continued)

*Primary Examiner* — Krishnan S Menon
*Assistant Examiner* — Dwan A Gerido
(74) *Attorney, Agent, or Firm* — Seager Tufte & Wickhem LLC.

(57) ABSTRACT

A hematology analyzer or cytometer cartridge system having flow metering. It may have on- or off-cartridge flow metering and control. The system may have local and direct flow measurement to provide accurate counts per unit volume. There may be numerous arrangements for fluidic circuit checks of the cartridge. Examples may include checks pertaining to zero flow, interface, pressure, flow rate, fluid type and quality, backflow, dry qualification, temperature exposure limits, and so on, of the circuits and cartridge associated items.

16 Claims, 15 Drawing Sheets

U.S. PATENT DOCUMENTS

| | | | |
|---|---|---|---|
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,315,861 A | 5/1994 | Egan et al. | |
| 5,323,999 A | 6/1994 | Bonne et al. | |
| 5,441,597 A | 8/1995 | Bonne et al. | |
| 5,452,878 A | 9/1995 | Gravesen et al. | |
| 5,457,526 A | 10/1995 | Kosaka | |
| 5,510,267 A | 4/1996 | Marshall | |
| 5,528,045 A | 6/1996 | Hoffman et al. | |
| 5,570,193 A | 10/1996 | Landa et al. | |
| 5,601,080 A | 2/1997 | Oppenheimer | |
| 5,616,501 A | 4/1997 | Rodriguez et al. | |
| 5,633,724 A | 5/1997 | King et al. | |
| 5,683,159 A | 11/1997 | Johnson | |
| 5,716,852 A | 2/1998 | Yager et al. | |
| 5,717,631 A | 2/1998 | Carley et al. | |
| 5,726,404 A | 3/1998 | Brody | |
| 5,726,751 A | 3/1998 | Altendorf et al. | |
| 5,757,476 A | 5/1998 | Nakamoto et al. | |
| 5,760,900 A | 6/1998 | Ito et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,839,807 A | 11/1998 | Perlo | |
| 5,863,502 A | 1/1999 | Southgate et al. | |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,924,294 A | 7/1999 | Tiby | |
| 5,932,100 A | 8/1999 | Yager et al. | |
| 5,939,326 A | 8/1999 | Chupp et al. | |
| 5,948,684 A | 9/1999 | Weigl et al. | |
| 5,970,315 A | 10/1999 | Carley et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,054,335 A | 4/2000 | Sun et al. | |
| 6,082,185 A | 7/2000 | Saaski | |
| 6,091,197 A | 7/2000 | Sun et al. | |
| 6,091,537 A | 7/2000 | Sun et al. | |
| 6,094,293 A | 7/2000 | Yokoyama et al. | |
| 6,097,485 A | 8/2000 | Lievan | |
| 6,097,859 A | 8/2000 | Solgaard et al. | |
| 6,106,245 A | 8/2000 | Cabuz | |
| 6,109,889 A | 8/2000 | Zengerle et al. | |
| 6,116,756 A | 9/2000 | Peeters et al. | |
| 6,124,663 A | 9/2000 | Haake et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,281,975 B1 | 8/2001 | Munk | |
| 6,382,228 B1 | 5/2002 | Cabuz et al. | |
| 6,537,501 B1 | 3/2003 | Holl et al. | |
| 6,549,275 B1 | 4/2003 | Cabuz et al. | |
| 6,576,194 B1 | 6/2003 | Holl et al. | |
| 6,597,438 B1 | 7/2003 | Cabuz et al. | |
| 6,691,113 B1 | 2/2004 | Harrison et al. | |
| 6,700,130 B2 | 3/2004 | Fritz | |
| 6,832,120 B1 | 12/2004 | Frank et al. | |
| 6,837,476 B2 | 1/2005 | Cabuz et al. | |
| 6,889,567 B2 | 5/2005 | Cabuz | |
| 6,970,245 B2 | 11/2005 | Fritz et al. | |
| 7,069,540 B1 | 6/2006 | Sievert | |
| 8,037,354 B2 | 10/2011 | Majewski et al. | |
| 2002/0127144 A1* | 9/2002 | Mehta | 422/81 |
| 2003/0083685 A1 | 5/2003 | Freeman et al. | |
| 2003/0142291 A1 | 7/2003 | Padmanabhan et al. | |
| 2004/0163464 A1* | 8/2004 | Nakada et al. | 73/204.26 |
| 2004/0202581 A1 | 10/2004 | Berndt | |
| 2004/0259241 A1 | 12/2004 | Barringer, Jr. | |
| 2005/0073686 A1 | 4/2005 | Roth et al. | |
| 2005/0105077 A1 | 5/2005 | Padmanabhan et al. | |
| 2005/0106739 A1 | 5/2005 | Cabuz et al. | |
| 2005/0106742 A1 | 5/2005 | Wahl | |
| 2005/0118723 A1 | 6/2005 | Padmanabhan et al. | |
| 2006/0139069 A1 | 6/2006 | Frank et al. | |
| 2012/0017115 A1 | 1/2012 | Majewski et al. | |

FOREIGN PATENT DOCUMENTS

| | | | |
|---|---|---|---|
| EP | 0269076 | | 6/1988 |
| EP | 1001326 | | 5/2000 |
| EP | 1134548 | | 9/2001 |
| EP | 2002243572 | | 8/2002 |
| JP | 61066947 | | 5/1986 |
| JP | 6316580 | | 7/1988 |
| JP | 331215 B2 | | 5/1991 |
| JP | 10073528 | | 3/1998 |
| JP | 2000056228 | | 2/2000 |
| JP | 2000266233 A | | 9/2000 |
| JP | 2002503331 A | | 1/2002 |
| JP | 2004505272 A | | 2/2004 |
| WO | 9527199 | | 10/1995 |
| WO | 9721090 A1 | | 6/1997 |
| WO | 9960397 | | 11/1999 |
| WO | 0109598 | | 2/2001 |
| WO | 0210713 | | 2/2002 |
| WO | 0210714 | | 2/2002 |
| WO | WO2004/079241 | * | 9/2004 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al, "Results Obtained Using a Prototype Microfluidics-Based Hematology Analyzer", SPIE Biomedical Optics 97, 1997.

Altendorf et al., "Differential Blood Cell Counts Obtained Using a Microchannel Based Flow Cytometer", Solid State Sensors & Actuators, vol. 1, 531, 1997.

Altendorf et al., "Implementation of Novel Optical Detection Methods for Clinically Important Blood Analytes Using Microfabricated Flow Structures (T-Sensors™)", MicroTAS 98, Banff, Canada, Apr. 1998.

Altendorf et al., "Microfabrication Technology for Research and Diagnostics, Silicon Microchannel Optical Flow Cytometry", SPIE Proceedings, Biomedical Optics 96, Jan. 1996.

Cabuz et al., "Mesoscopic Sampler Based on 3D Array of Electrostatically Activated Diaphragms", The 10th Int. Conf. on Solid-State Sensors and Actuators, Transducers'99, p. 1890-1, Sendai Japan, Jun. 7-12, 1999.

Darling et al., "Integration of Microelectrodes With Etched Microchannels for In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

Hatch et al., "Microfluidic Approaches to Immunoassays", SPIE conference on Micromachining and Microfabrication Symposium at Santa Clara, CA, Sep. 20-22, 1999.

"Liquid Flow Sensors," Honeywell, 2 pages, 2004.

"Liquid Flow Sensors 5nL/min to 5µL/min Flow Range, X116161-AW," Honeywell, 2 pages, 2004.

Huang et al., "Development of a Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, p. 237, 1995.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3rd International Conference on Micro Opto Electro Mechanical Systems (MOEMS 99), Aug. 30-Sep. 1, 1999, Mainz, Germany, pp. 165-170.

Toshiyoshi et al., "Surface micromachined 2D Lens Scanner Array", Proc. IEEE?LEOS International Coference on Optical EMMS/Sheraton Kauai Resort, Kauai, Hawaii, Aug. 21-24, 2000, 3 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array for Beam Steering and Precision Alignment in Optical Interconnect Systems", Solid-State Sensor and Actuator Workshop, Hilton Head Island, South Carolina, Jun. 4-8, 2000, pp. 101-104.

Weigh et al, "Silicon-Microfabricated Diffusion-Based Optical Chemical Sensor", Reprint from "Sensors & Actuators" B 38-39, 452-457, 1997.

Weigl et al, "Microfluidic Diffusion-Based Separation and Detection", Science, vol. 283, pp. 346-347, Jan. 15, 1999.

Weigl et al, "Optical and Electrochemical Diffusion-Based Detection of Analytes in Complex Samples Using Microfabricated Flow Structures (T-SensorSTM)", Micro- and nanofabn'cated electro-optical mechanical systems for biomedical and environmental applications II—SPIE vol. 3606, Jan. 25-26, 1999.

Weigl et al, "Simultaneous Self-Referencing Analyte Determination in Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection in Silicon Flow Structures", B. Weigl et al., Analytical Methods & Instrumentation, μTTAS 96 special edition, 1996.

Weigl et al., "Fluorescence and Absorbance Analyte Sensing in Whole Blood and Plasma Based on Diffusion Separation in Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", μTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Yager et al., "Applying Microfluidic Chemical Analytical Systems to Imperfect Samples", Micro Total Analysis Systems 98, D. Harrison & A. van den Berg (ed.), Kluwer Academic Publishers, Dordrecht, 207-212, 1998.

Yager et al., "Design of Microfluidic Sample Preconditioning Systems for Detection of Biological Agents in Environmental Samples", Yager, M. et al., SPIE Proceedings, 3515, 252-259, 1998.

AX, "The Cost to Build Device-to-Enterprise Solutions Just Went Down . . . AXponentially", 8 pages, prior to Sep. 18, 2008.

Tridium, "Vycon JACE-200", 2 pages, 2007.

Tridium, "Vycon JACE-600", 2 pages, 2007.

Tridium, Niagara Architecture Overview, 5 pages, Copyright 2000-2007.

Tridium, Niagara Component Model, 2 pages, Copyright 2000-2007.

* cited by examiner

FLOW METERED ANALYZER

The present invention claims the benefit of U.S. Provisional Patent Application No. 60/696,162, filed Jul. 1, 2005. U.S. Provisional Patent Application No. 60/696,162, filed Jul. 1, 2005, is hereby incorporated by reference.

BACKGROUND

The present invention pertains to analyzers and particularly to flow metering in analyzers. More particularly, the invention pertains to flow metering in hematology analyzers and flow cytometers.

Patents and applications related to the present invention may include: U.S. Pat. No. 6,382,228, issued May 7, 2002, and entitled "Fluid Driving System for Flow Cytometry"; U.S. Pat. No. 6,597,438, issued Jul. 22, 2003, and entitled "Portable Flow Cytometry"; U.S. Pat. No. 6,970,245, issued Nov. 29, 2005, and entitled "Optical Alignment Detection System; U.S. Pat. No. 6,549,275, issued Apr. 15, 2003, and entitled "Optical Detection System for Flow Cytometry"; U.S. Pat. No. 5,836,750, issued Nov. 17, 1998, and entitled "Electrostatically Actuated Mesopump Having a Plurality of Elementary Cells"; U.S. patent application Ser. No. 11/027,134, filed Dec. 30, 2004, and entitled "Optical Detection System with Polarizing Beamsplitter; U.S patent application Ser. No. 10/908,543, filed May 16, 2005, and entitled "Cytometer Analysis Cartridge Optical Configuration"; and U.S. patent application Ser. No. 10/908,014, filed Apr. 25, 2005, and entitled "A Flow Control System of a Cartridge"; all of which are hereby incorporated by reference.

SUMMARY

The present invention may involve direct flow monitoring and measuring of portions of hematology analyzers and cytometers improving the accuracy of certain items such as blood counts per unit volume. Also, various checks of the analyzers or cytometers may be effected.

DESCRIPTION

Figure 1:
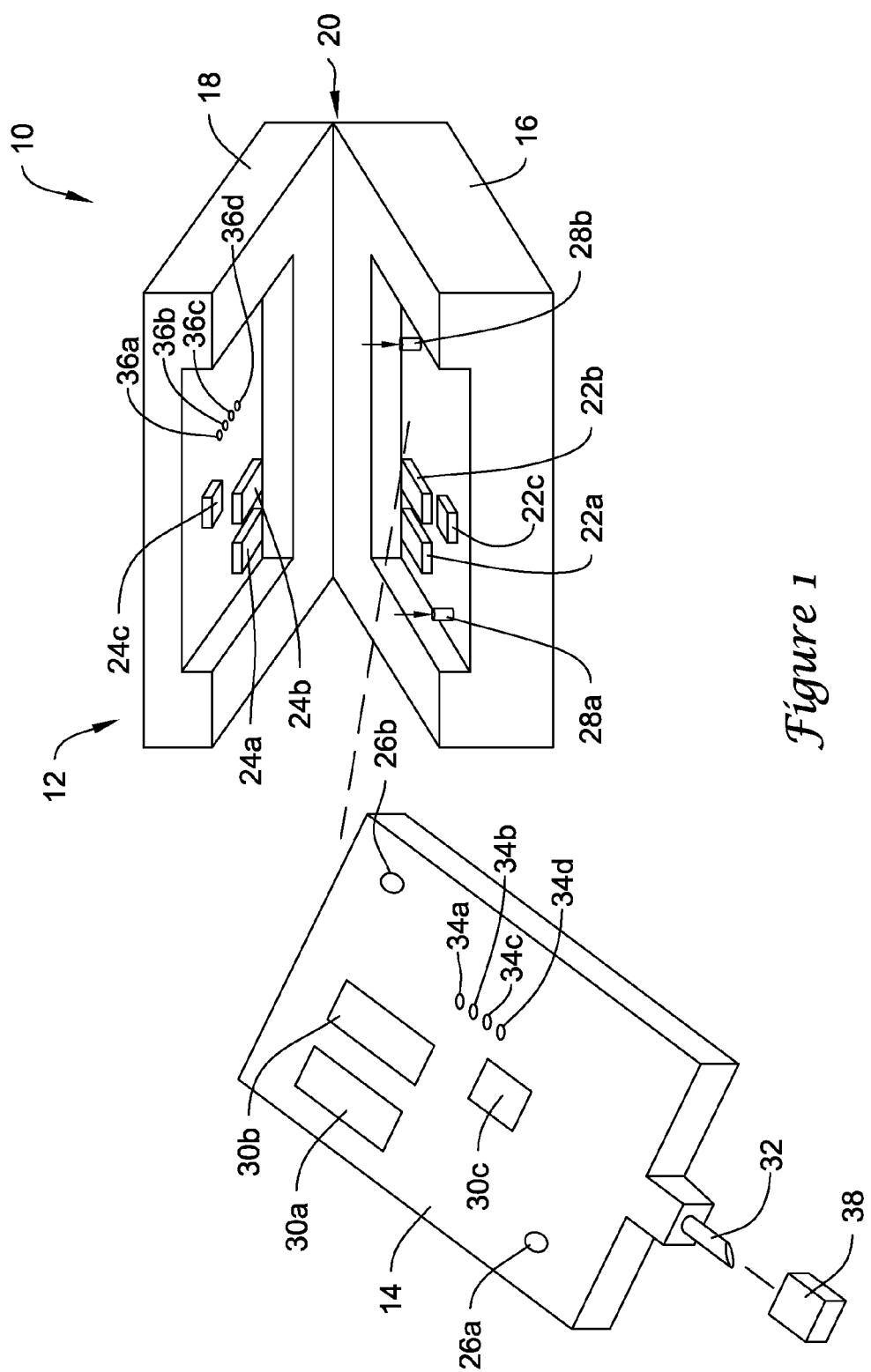
FIG. 1 is a block diagram of a particle counting and size measurement system.

The present invention generally relates to sample analyzers, and in particular, to sample analyzers with removable and/or disposable cartridges for use at the point of care of a patient such as in a doctor's office, in the home, or elsewhere in the field. By providing a removable and/or disposable cartridge with all of the needed reagents and/or fluids, the sample analyzer can be reliably used outside of the laboratory environment, with little or no specialized training. This may, for example, help streamline the sample analysis process, reduce the cost and burden on medical or other personnel, and increase the convenience of sample analysis for many patients, including those that require relatively frequent blood monitoring/analysis.

An approach which permits rapid and efficient particle discrimination in a particle-suspension sample is flow cytometry. In this approach, a suspension of particles, typically cells in a blood sample, may be transported through a flow channel where the individual particles in the sample are illuminated with one or more focused light beams. The interaction of the light beam(s) with the individual particles flowing through the flow channel may be detected by one or more light detectors. Commonly, the detectors may be designed to measure light absorption or fluorescence emission, at specific beam or emission wavelengths, and/or light scattering at specific scattering angles. Thus, each particle that passes through the flow channel may be characterized as to one or more features related to its absorption, fluorescence, light scattering or other optical or electrical properties. The properties that are measured by the detectors may allow each particle to be mapped into a feature space whose axes are the light intensities or other properties which are measured by the detectors. In an ideal approach, the different particles in the sample map into distinct and non-overlapping regions of the feature space, allowing each particle to be analyzed based on its mapping in the feature space. Such analysis may include counting, identifying, quantifying (as to one or more physical characteristics) and/or sorting of the particles.

In one illustrative example may be a sample analyzer which is provided that has a removable cartridge that receives a collected sample, such as a collected whole blood sample, and once the removable cartridge is installed and the analyzer is activated, the analyzer and cartridge may automatically process the sample and the analyzer may provide sufficient information for the user to make a clinical decision. In some examples, the analyzer displays or prints out quantitative results (e.g., inside and/or outside of a predefined range), such that no further calculations or interpretation is required by the user.

The sample analyzer may be used to, for example, determine the number and/or types of white blood cells in a blood sample. In one illustrative example, the analyzer includes a housing and a removable fluidic cartridge, wherein the housing is adapted to receive the removable fluidic cartridge. In some cases, the removable fluidic cartridge is a disposable cartridge. In an illustrative example, the removable fluidic cartridge may include one or more reagents (e.g., sphering agents, lysing reagents, stain, and/or diluents, one or more analysis channels, one or more flow sensors, one or more valves, and/or a fluidic circuit that is adapted to process (e.g., sphere, lyse, stain, or other) a sample and deliver processed sample(s) to the appropriate analysis channel on the cartridge.

To support the card, the housing may include, for example, a pressure source, one or more light sources, one or more light detectors, a processor and a power source. The pressure source may provide appropriate pressure(s) to the removable fluidic cartridge ports to drive the fluids as required through the fluidic circuit. The one or more light sources of the analyzer may be used to interrogate the prepared sample in at least selected analysis channels of the removable cartridge, and the one or more light detectors of the analyzer may detect the light that passes through, is absorbed by and/or is scattered by the sample. The processor may be coupled to at least some of the light sources and detectors, and may determine one or more parameters of the sample. In some examples, the one or more analysis channels on the removable fluidic cartridge may include one or more flow cytometry channels. In some illustrative examples, a whole blood sample may be provided to the removable fluidic cartridge, and the removable cartridge may be adapted to perform a blood analysis.

FIG. 1 is a perspective view of an illustrative sample analyzer 10 and cartridge 14. The illustrative sample analyzer 10 may include a housing 12 and the removable or disposable cartridge 14. The illustrative housing 12 may include a base 16, a cover 18, and a hinge 20 that attaches the base 16 to the cover 18, but this is not required. In the illustrative example, the base 16 includes a first light source 22a, a second light source 22b, and a third light source 22c, along with associated optics and the necessary electronics for operation of the sample analyzer. There may be more or less light sources. Each of the light sources may be a single light source or multiple light sources, depending on the application. In some cases, the overall dimensions of the housing may be significantly less than one-quarter cubic foot. Likewise, the overall weight of the housing may be significantly less than less than one pound.

The illustrative cover 12 may include a pressure source (e.g., pressure-chambers with control microvalves), a first light detector 24a, a second light detector 22b, and a third light detector 22c, each with associated optics and electronics. There may be more or less detectors. Each of the light detectors may also be a single light detector or multiple light detectors, depending on the application. Polarizers and/or filters may also be incorporated, depending on the application.

The illustrative removable cartridge 14 may be adapted to receive a sample fluid via a sample collector port, which in the illustrative example, includes a lancet 32. The lancet 32 may be retractable and/or spring loaded, in some examples. A cap 38 may be used to protect the sample collector port and/or lancet 32 when the removable cartridge 14 is not in use.

In the illustrative example, the removable cartridge 14 may perform a blood analysis on a whole blood sample. The lancet 32 may be used to prick the finger of the user to produce a sample of blood, which through capillary action, may be drawn into an anti-coagulant coated capillary in the removable cartridge 14. The removable cartridge 14 may be constructed with fluidic circuits, some of which are fabricated using a laminated structure with etched channels. However, it is contemplated that the removable cartridge 14 may be constructed in any suitable manner including by injection molding or any other suitable manufacturing process or method.

During use, and after a blood sample has been drawn into the removable cartridge 14, the removable cartridge may be inserted into the housing when the cover 18 is in the open position. In some cases, the removable cartridge 14 may include holes 26a and 26b for receiving registration pins 28a and 28b in the base 16, which may help provide alignment and coupling between the different parts of the instrument. The removable cartridge 14 may also include a first transparent flow stream window 30a, a second transparent flow stream window 30b and a third transparent window 30c, which are in alignment with the first, second and third light sources 22a, 22b and 22c, and the first, second and third light detectors 24a, 24b and 24c, respectively.

When the cover is moved to the closed position, and the system is pressurized, the cover 18 may provide controlled pressures via pressure providing ports 36a, 36b, 36c, and 36d to pressure receiving ports 34a, 34b, 34c and 34d, respectively, in the illustrative removable cartridge 14. It is contemplated that more or less pressure providing and pressure receiving ports may be used, depending on the application. Alternatively, or in addition, it is contemplated that one or more micro-pumps, such as electrostatically actuated meso pumps, may be provided on or in the removable cartridge 14 to provide the necessary pressures to operate the fluidic circuit on the removable cartridge 14. Some illustrative electrostatically actuated meso pumps may be described in, for example, U.S. Pat. Nos. 5,836,750, 6,106,245, 6179,586, 6,729,856, and 6,767,190, all of which are hereby incorporated by reference. Once pressurized, the illustrative instrument may perform a blood analysis on the collected blood sample.

The present system may provide a complete blood count (CBC) card based on a micro-scale flow cytometer or hematology analyzer for obtaining one or more of the following items including red blood cell (RBC) counts, sphering RBCs, platelet counts, lysis of RBCs, multi-part differential counts of white blood cells (WBCs), hemoglobin absorbence-based measurements, various additional indices of RBCs, platelets, WBCs, hemoglobin, and so forth, plus hydrodynamic focusing to create single-file streams of cells, and a pneumatic fluid driver system. Additional items may be provided by and/or be a part of the present system. A cytometer and a hematology analyzer might be regarded as the same or similar systems.

Figure 2:
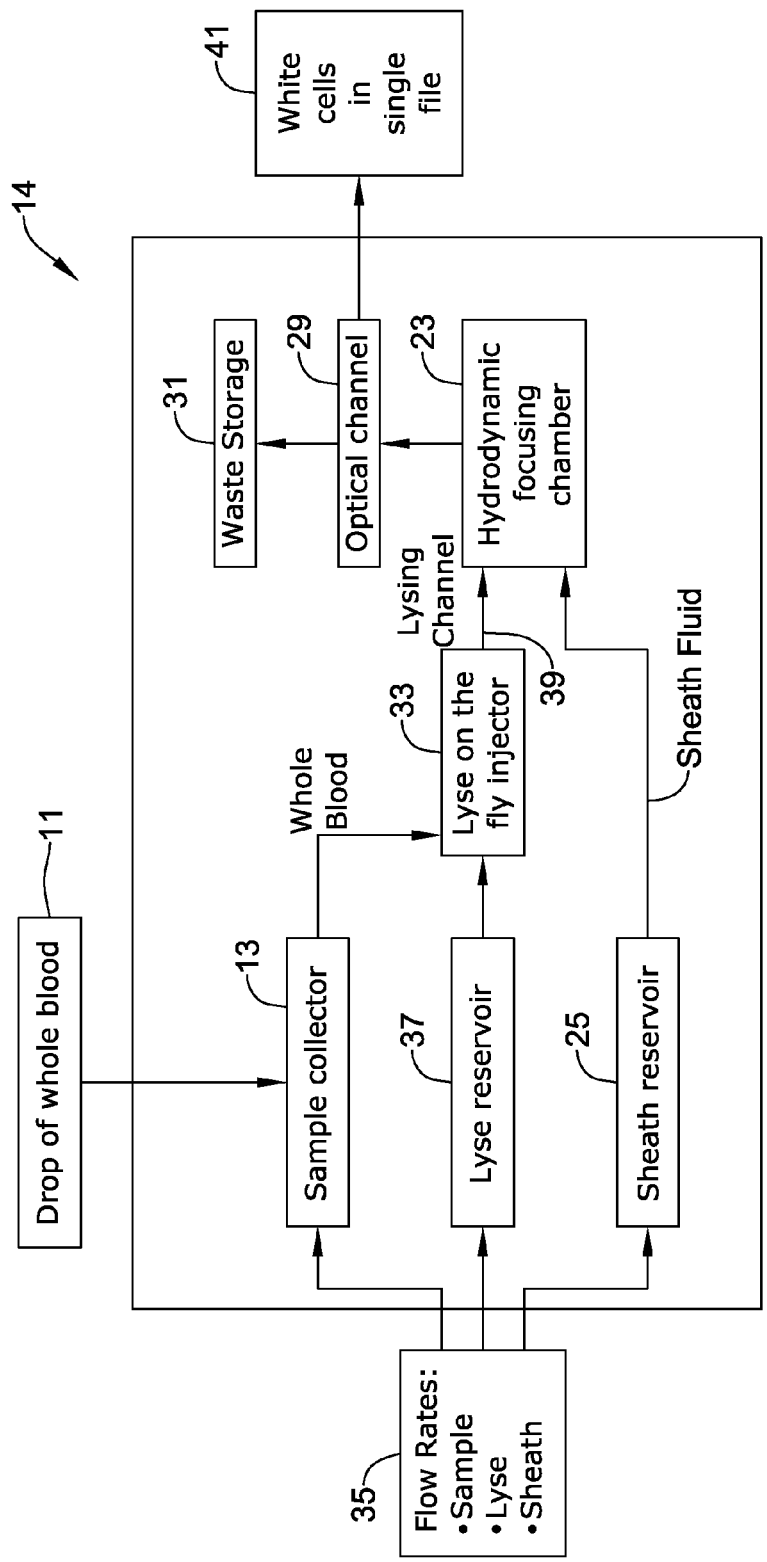
FIG. 2 shows a portion of an illustrative blood analysis cartridge for white blood cells.

FIG. 2 is a diagram showing some aspects of an illustrative example of a WBC portion of cartridge or card 14. One may start with a sample of whole blood 11 to a sample collator 13. The blood may be pushed on to a lyse on the fly injector 33. The flow rates for pushing the sample, and also the lysing and sheath fluids may be provided by a pump mechanism or flow rate control box 35. Lysing fluid for the lyse on the fly injector may come from a lyse reservoir 37. The lyse fluid and blood may proceed through a lysing channel 39 to a hydrodynamic focusing chamber 23. A sheathing fluid may go from a sheath reservoir 25 to the hydrodynamic focusing chamber 23 to aid in aligning white cells in a single file 41 through an optical channel 29 for detection and analysis. After the cells have proceeded to optical channel 29, the cells and fluid may move to a waste storage 31.

Figure 3:
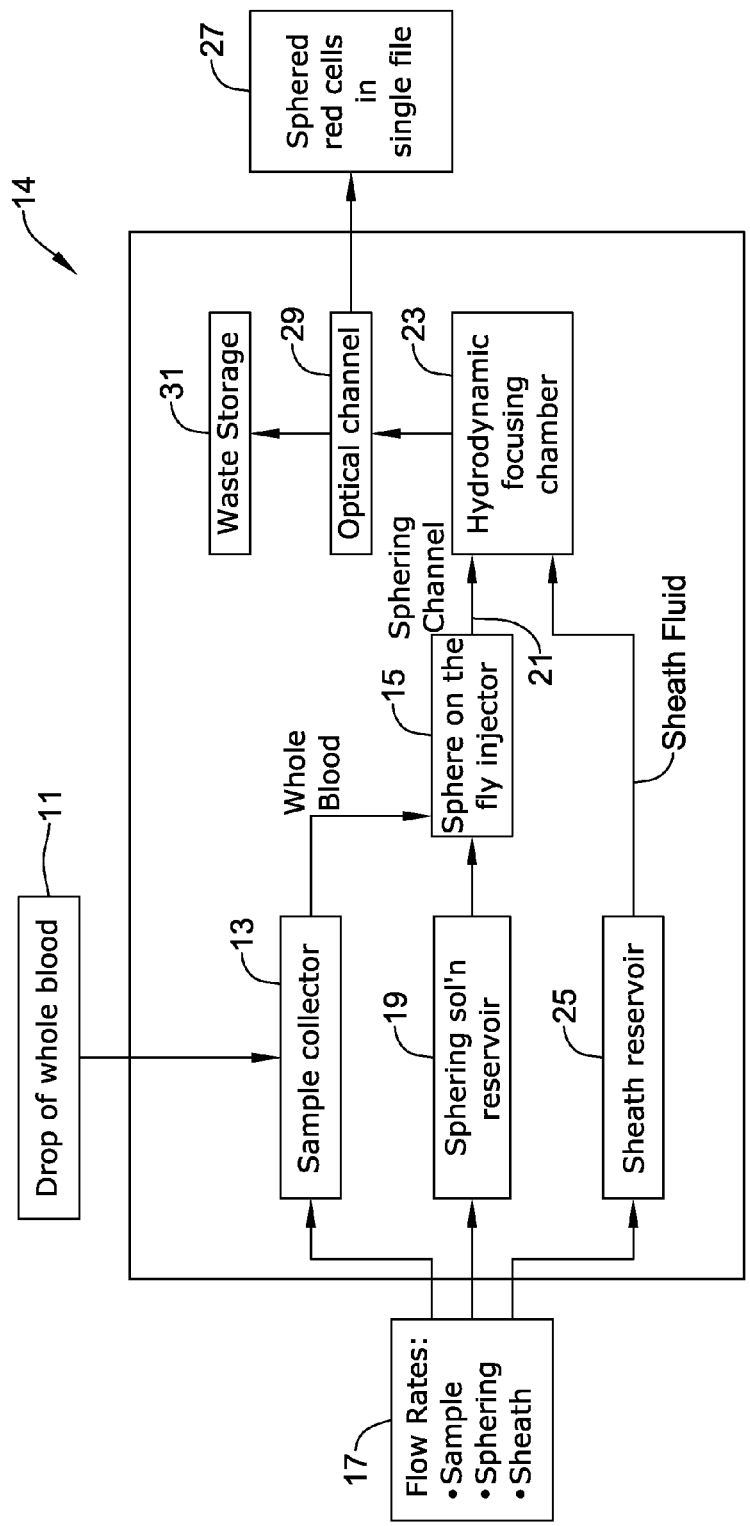
FIG. 3 shows a portion of the an illustrative blood analysis cartridge for red blood cells.

FIG. 3 is a diagram showing some of the aspects of an illustrative example of an RBC portion of cartridge or card 14. This card 14 may be similar to the WBC card 14 except that it may be designed for RBC analysis. Similarly, instrument 10 may be designed for RBCs. One may start with a sample of whole blood 11 going to a sample collector 13. The blood may be pushed to a sphere on the fly injector 15. The flow rates for pushing the sample, and also for the sphering and sheath fluids, may be provided by a pump mechanism or flow rate control box 17. Sphering fluid for the sphere on the fly injector 15 may come from a sphering solution reservoir 19. The solution and blood may proceed through a sphering channel 21 to a hydrodynamic focusing chamber 23. A sheathing fluid may go from a sheath reservoir 25 the hydrodynamic focusing chamber 23 to aid in aligning the sphered red cells in single file 27 through an optical channel 29 for detection and analysis. After the cells have proceeded through optical channel 29, the cells and fluid may move on to a waste storage 31.

Figure 4:
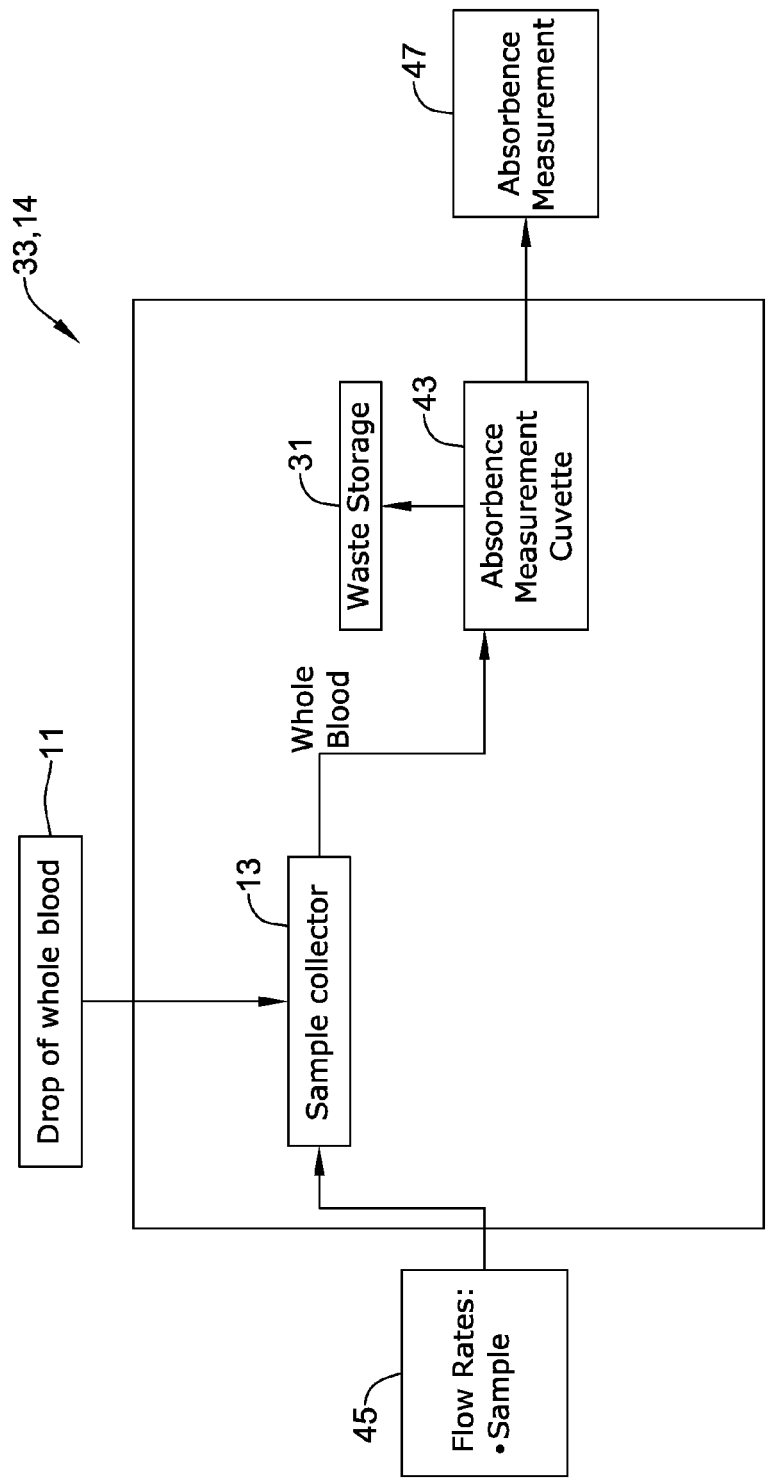
FIG. 4 shows a portion of the illustrative blood analysis cartridge for hemoglobin.

FIG. 4 is a diagram showing some aspects of an illustrative example of a hemoglobin (HGB) card 33 or HGB portion of cartridge or card 14. This card may be a substitute for the WBC card 14 except it is designed for HGB analysis. Similarly, instrument 10 may be designed for HGB measurement. One may start with a sample of whole blood 11 to a sample collector 13. The blood may be pushed on to an absorbence measurement cuvette 43. The flow rate for pushing the sample may be provided by a pump mechanism or flow rate control box 45. The blood may proceed through the absorbence measurement cuvette 43, which may provide an absorbence measurement 47. After the measurement, the blood may proceed on to a waste storage 31.

Hematology analyzers and flow cytometers (viz., analyzers) may use syringe pumps in open loop and do not measure flow rates of the various reagents and drive fluids. The use of a flow sensor in such analyzers may be useful to improve overall analyzer system accuracy. Direct and local measurements of flow may provide a basis for obtaining more precise and accurate flow rates and blood counts per unit volume with the present system. Miniaturized hematology analyzers that use disposable analysis cards may need flow sensors to allow for flow rate volume error compensation. This would be essential towards developing a hematology analyzer for providing tests that may be waived under the Clinical Laboratory Improvement Amendments of 1988 (CLIA) law. An analyzer capable of providing such waived tests will need self-diagnostics capabilities to check, detect and correct for bubbles, flow leaks, occlusions, and so on.

Development of a miniaturized, low cost, ultrasensitive and stable liquid flow sensor may permit the measurement of flow rates and flow volume (dose) in hematology analyzers. The use of a flow sensor in conjunction with a closed loop pumping system may permit compensation for flow rate errors and changes. The flow sensor may also be as an instrumentation diagnostics sensor for detecting bubbles, occlusions, and flow leaks by being appropriately positioned in the instrument or in the disposable card. A flow sensor capable of measuring very slow flow rates, having a small volume and using little power for the present invention is noted herein.

There has been an increasing need for accurate measurement of the flow rates of fluids (i.e., liquids and gases) for medical, industrial, life sciences and commercial applications. The desired flow rates may range from nL/min for drug delivery, life sciences analytical instrumentation, and robotic liquid handling systems to mL/min or even liters/min for dialysis machines and other industrial applications. The present microfluidics applications may use some form of precision fluid metering or fluid dosing that needs to be accomplished by sensors that are ultra small (chip size less than 25 mm$^2$), that consume low power (less than 75 mW), with high accuracy (better than 2 percent), and fast response speeds (faster than 1 millisecond).

Flow rate may be measured using either a direct or indirect measurement technique. Flow rate has been measured indirectly usually by measuring static properties and then making a calculation. A classic method is to measure the amount of time required to fill a known volume. The greatest advantage of this approach is that the static properties may be known with great precision and be traceable to international standards. The calculations are simple and based on proven physical laws, so confidence in the result is high. There are disadvantages of this approach. A significant one may be the inability to know much about flow rates that vary with time. Additionally, faster measurements may have poorer precision. Thus, this technique is best suited where flow rates are constant (or where average flow is the desired output) and where response time/speed is not an issue.

Another method of indirect flow measurement may use the principle that flow in a confined space is proportional to a pressure drop. A differential pressure sensor may be used to measure pressure drop over a constriction, which includes the restriction due to a length of pipe. This method may overcome the limitations (in time-volume methods) of varying flow rates and long response times but at the expense of more complex calculations, larger potential external errors and larger perturbations of the media. Greater precision may be obtained by smaller restriction, but that directly changes flow characteristics.

There has been increasing interest in measuring very low flows on a practical, outside the laboratory, basis. For gases this may be less than 1 Liter per minute and for liquids less than 1 μL per minute. The errors inherent to the indirect methods may be greatly magnified at these low flows while the signals are reduced. To avoid such issues, direct measurement of flow rate may be provided in the present system.

Figure 5:
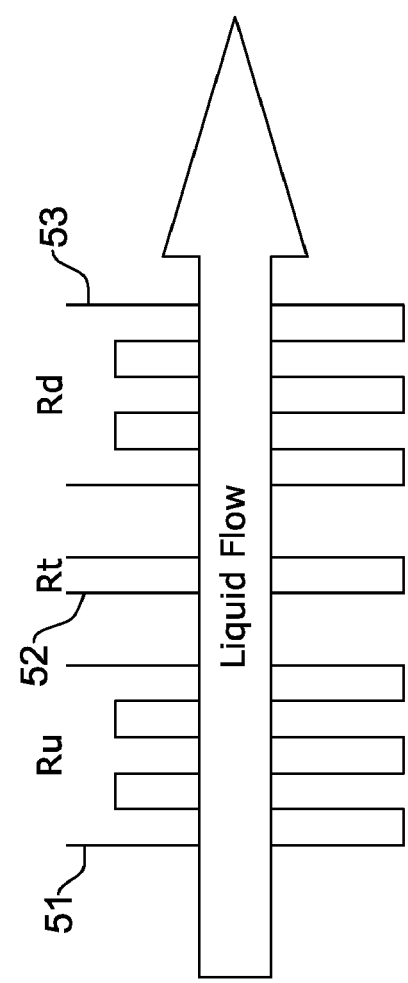
FIG. 5 is a diagram of a flow sensor used for in the present system.

A liquid flow sensor may use proven micro electromechanical systems (MEMS) technology to deliver fast and accurate flow rate measurements, including those of very small rates, in a very small package size. As shown in FIG. 5, such flow sensor may use a thermal-based technology where the thermally isolated heater (Rt) 51 is heated above ambient and where liquid flow is proportional to the temperature difference between the upstream (Ru) 52 and downstream (Rd) 53 temperature sensors located on either side of the heater. Calibration curves for the sensor may vary depending on the thermal conductivity of the liquid.

An example flow sensor may be specifically designed for applications requiring accurate flow measurements at extremely low flow rates from 1 nL/min to 50 μL/min. This sensor may be used for feedback control loops operating in this region. The sensor may feature fast response time and automatic temperature compensation. This flow sensor may use MEMS-based thermal anemometry technology to measure the mass flow rate of liquids of an isolated flow channel. Such sensor may be available from Honeywell International Inc. of Morristown, N.J. Other similar flow sensors and also appropriate pressure sensors may be available from this company.

Figure 6:
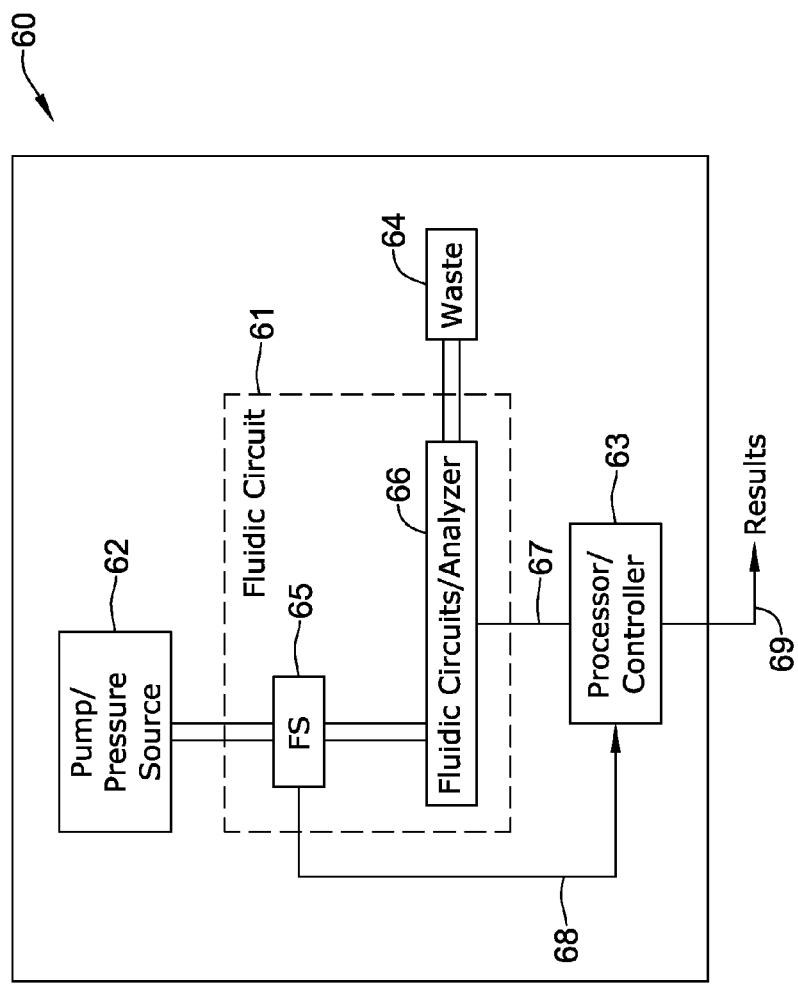
FIG. 6 is a block diagram with flow sensing for compensating processor outputs of the hematology analyzer.

FIG. 6 is a diagram of an example analyzer system 60 (e.g., a cytometer or hematology analyzer), having a fluidic circuit 61, a pump pressure source 62 connected to a flow sensor 65, and a processor/controller 63 and a waste reservoir 64 connected to the fluid circuits/analyzer 66. The fluidic circuit 61 includes the flow sensor 65 connected the fluid circuits/analyzer 66. This arrangement may permit local and direct flow rate measurements. Source 62 may provide a fluid through the flow sensor 65 to the fluid circuits/analyzer 66. Signals 67 about the fluid may go from analyzer 66 to the processor/controller 63. A signal 68 indicating a rate of fluid flow to the analyzer 66 may go from flow sensor 65 to processor 63. Results from the signals 67 from analyzer 66 to processor 63 may be corrected as a function of the sensed flow rate from flow sensor 65. Processor 63 may then output corrected results 69, which may include blood counts, such as the number of cells per unit volume.

Figure 7:
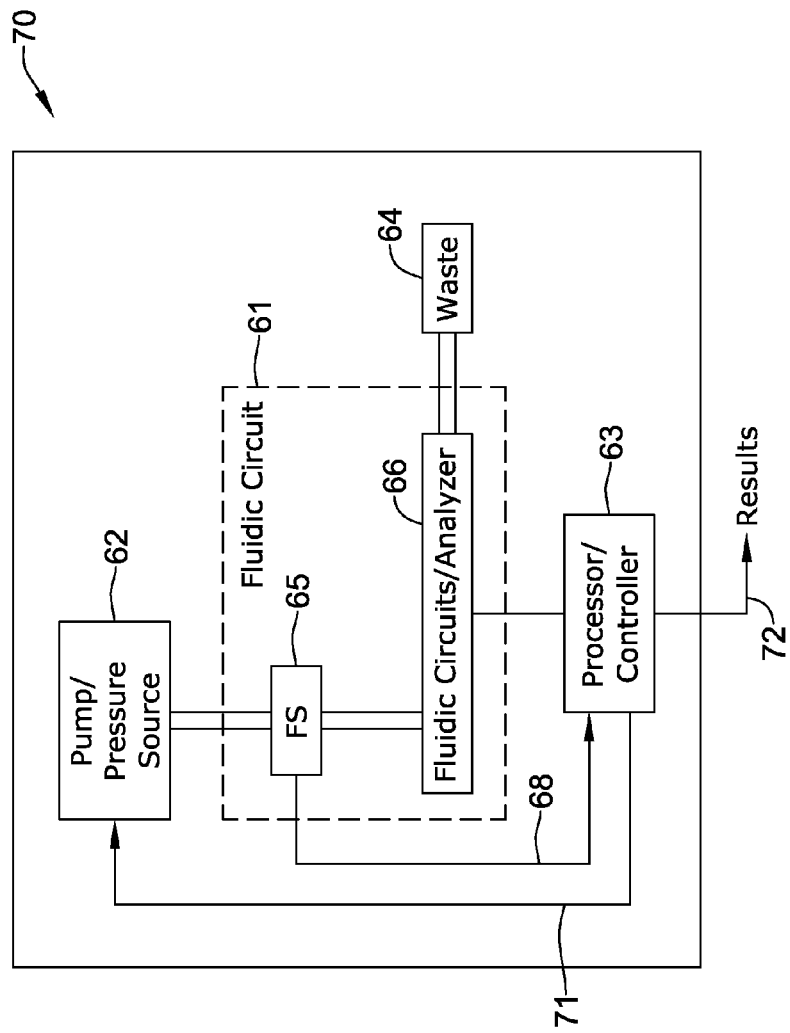
FIG. 7 is a block diagram with flow sensing and a closed loop to control flow to the hematology analyzer.

FIG. 7 is a diagram of an example analyzer system 70 (e.g., a cytometer or hematology analyzer), having similar components as analyzer system 60, also permitting local and direct flow rate measurements. However, processor 63 may provide a feedback signal 71 to the pump/pressure source 62 resulting in closed loop control of the flow rate provided by the pump/ pressure source 62 as sensed by the flow rate sensor 65 via signal 68. Processor 63 may then provide results 72 based on the closed loop control, which may include blood counts, such as the number of cells per unit volume.

A purpose of the present system, 60 and 70, with the local and direct measurements of the flow sensor, is to obtain accurate counts per unit volume. For instance, an optical portion of the system may provide a number of cells per second from a sample. This datum may be divided by the present flow sensor output, for instance, in microliters per second to obtain cells per microliter.

Figure 8:
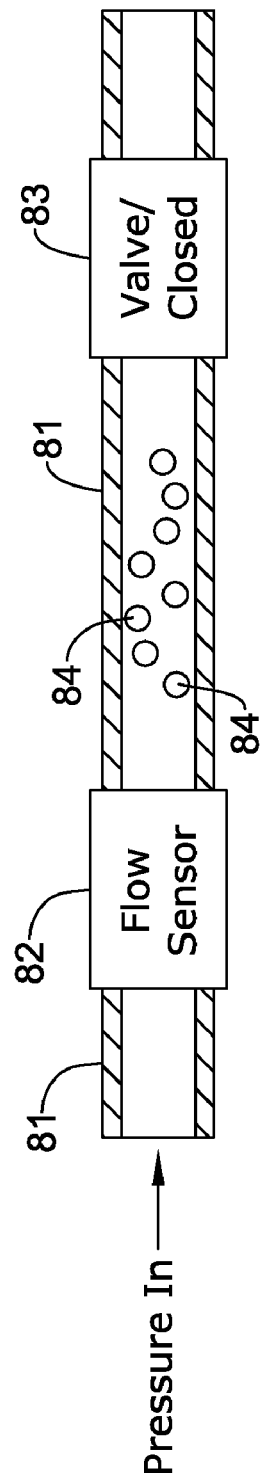
FIG. 8 shows a setup for a zero flow check of a closed off channel.

FIG. 8 shows an approach for a zero flow check. A fluid, e.g., a liquid, may be injected to a channel 81 at a pressure$_{IN}$. There may be a flow sensor 82 in the channel 81. Further down the channel may be a value 83 which is closed. With valve 83, a flow rated detected by flow sensor 82 upon application of pressure an input of channel 82 filled with a liquid should be zero. If the sensor 82 does not read zero at that time, then there may be bubbles 84 or leak(s) present in the channel. This check may assume the walls of channel 81 to be relatively non-compliant, e.g., stiff.

Figure 9:
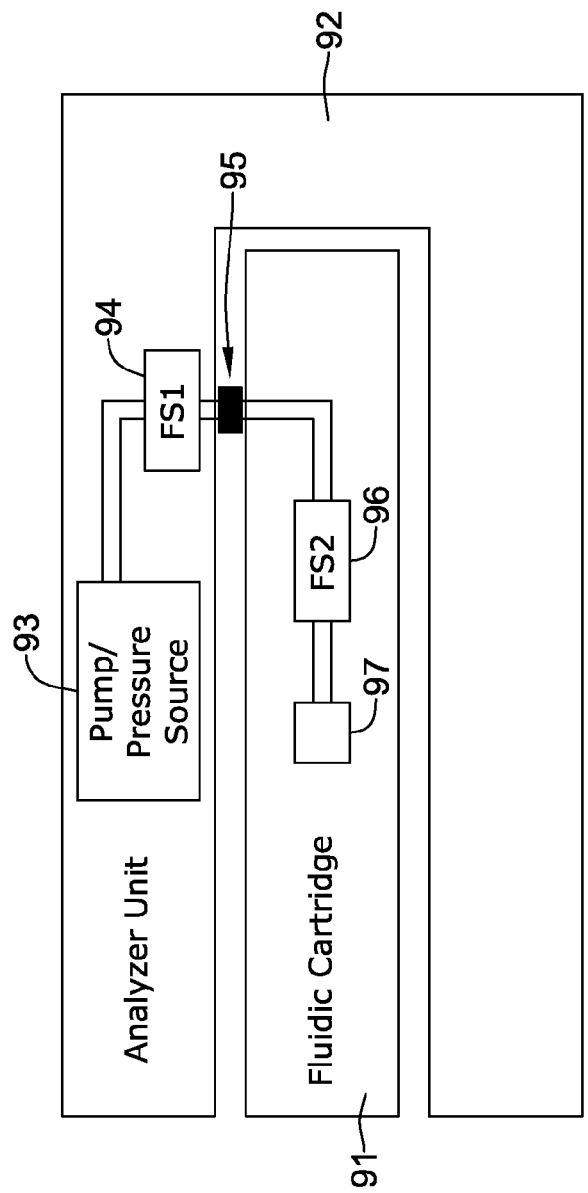
FIG. 9 shows a setup for an analyzer and cartridge interface check.

FIG. 9 shows an approach for an interface leak between an analyzer unit 91 and a fluidic cartridge 92. There may be a pump/pressure source 93 having an output connected to a flow sensor 94 which in turn is connected to an interface 95 between the analyzer 93 and the cartridge 91. A flow sensor 96 may be connected between a fluidic circuit 97 and the interface 95. A flow rate detected by flow sensor 94 should match a flow rate detected by flow sensor 96 unless a leak is present at the interface 95.

Figure 10:
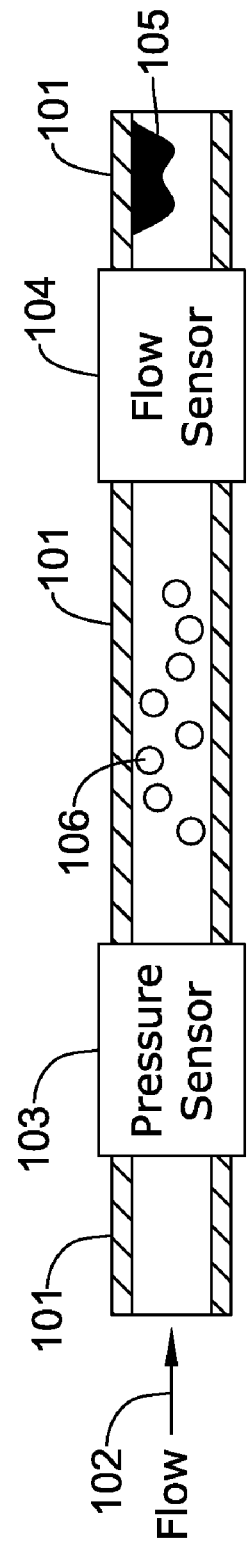
FIG. 10 shows a setup for a pressure and/or flow rate check for a fluidic circuit.

FIG. 10 shows an approach for a pressure/flow rate check. A channel 101 may have an input flow 102. A pressure sensor 103 and a flow sensor 104 may be placed in channel 101. A ratio of a pressure detected by the pressure sensor 103 and a flow rate detected by the flow sensor 104 should be within a predetermined range unless there is a partial or full blockage 105, bubbles 106 or other anomaly in the channel 101.

Figure 11:
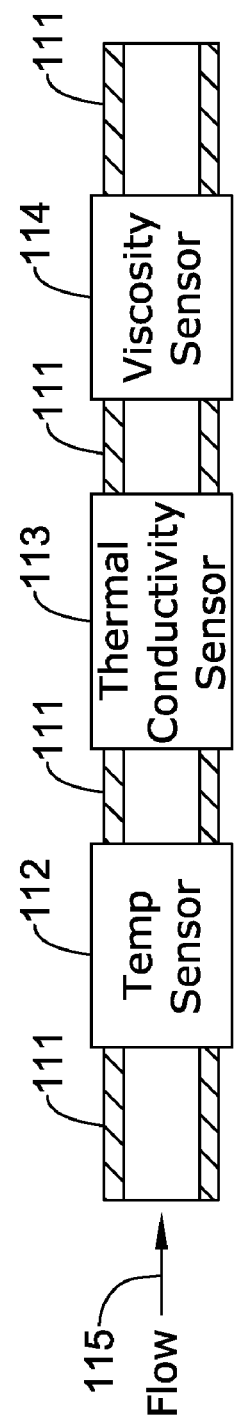
FIG. 11 shows a sensor setup for a fluid type and quality check.

FIG. 11 shows an approach for a fluid check. A flow channel 111 may have a temperature sensor 112, a thermal conductivity sensor 113 and a viscosity sensor 114 in place. A flow 115 of fluid may be entered into channel 111. The temperature, thermal conductivity, viscosity and other properties, as indicated by sensors 112, 113, 114 and other sensors, of the fluid passing through the flow channel 111 may be detected, and with pertinent calculations, the fluid type and its properties should be as expected. If not, then the fluid may be of an improper type, may have absorbed humidity, may have bacteria growth in it, may not be properly mixed, may have salts settled out, may have deteriorated due to expired shelf life, and/or so on.

Figure 12:
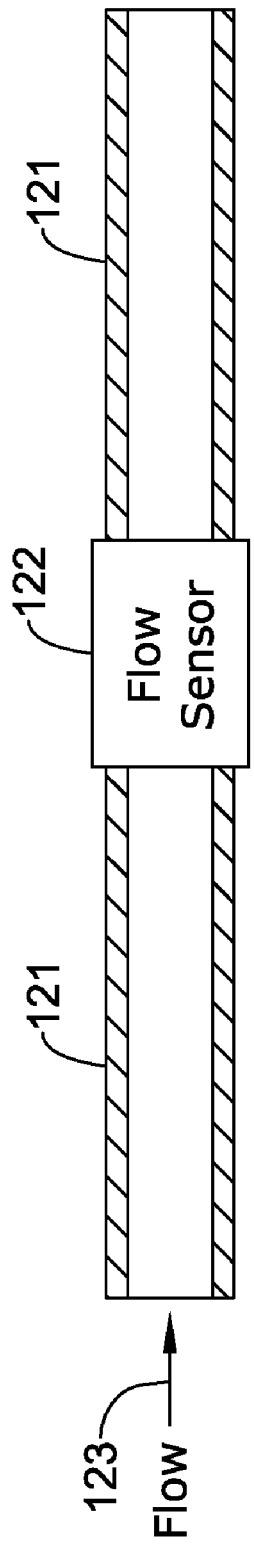
FIG. 12 shows a setup for a backflow check.

FIG. 12 shows an approach for a backflow check. There may be a channel 121 in a fluidic circuit. A flow sensor 122 may be placed in the channel 121 with a flow 123 going through the channel. The flow sensor 122 may detect backflow in the sensor 122, which in many cases, may be undesirable.

Figure 13:
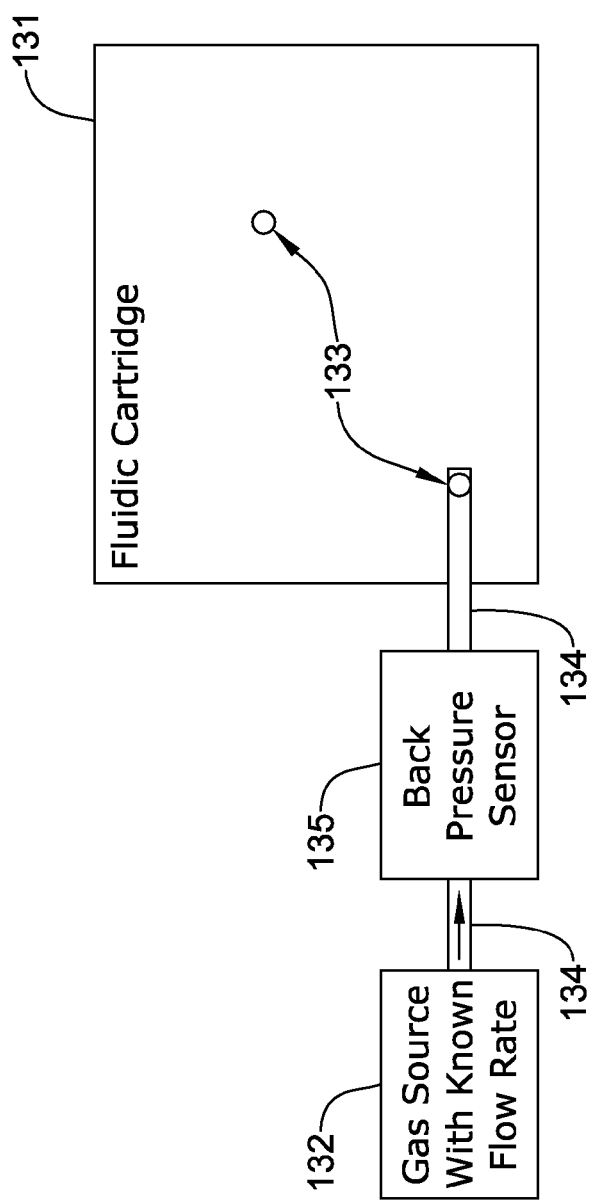
FIG. 13 shows a setup for a dry qualification of a fluidic cartridge.

FIG. 13 shows an approach that may be used for a dry qualification of a fluidic cartridge 131. There may be a gas source 132 connected to a port 133, the fluidic cartridge 131 via a channel or tube 134, and a backpressure sensor 135. The gas source 132 may pump a known flow rate of gas, such as nitrogen, into a port 133 of the fluidic cartridge 131. The measured backpressure, as indicated by sensor 135, may be determined as to whether it is within a specified "good" range. The gas source 132 may pump a known pressure of gas, such as nitrogen, into a port 133 of the fluidic cartridge 131, and with a flow rate sensor in place of pressure sensor 135, one may determine whether a measured flow rate is within a specified "good" range.

Figure 14:
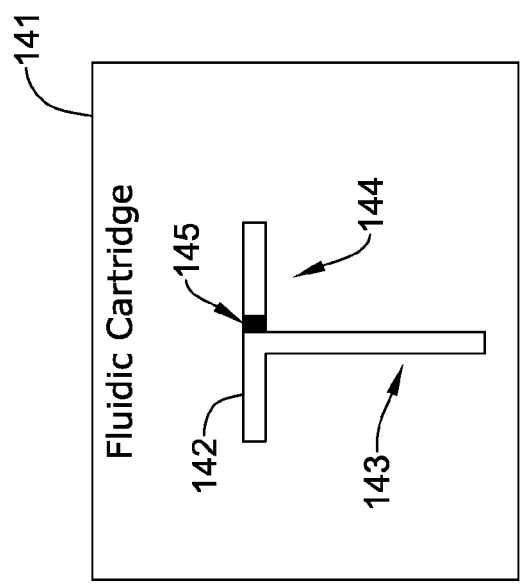
FIG. 14 shows a setup for a temperature exposure limits check for a fluidic circuit.

FIG. 14 shows an approach for doing a temperature exposure limits check. In a fluidic cartridge 141 circuit, there may be an input channel 142 connected to a normal flow channel 143 and to a bypass channel 144. Placed at an entry of the bypass channel 144 may be a blocking wax, or other suitable material, temperature fuse 145. One may use this approach to determine whether the fluidic cartridge 141 has been exposed to temperatures outside of specified temperature exposure limits. As to a high temperature limit check, the temperature fuse 145 may open up the entry of the bypass channel 145 (e.g., by melting of the wax) when the cartridge 141 is exposed to a temperature above the high temperature limit. This opening of the bypass channel 145 may cause an error detectable by a cartridge analyzer when the cartridge 141 is inserted into the analyzer.

As to a flow temperature limit, the temperature fuse 145 may involve water or other suitable material, such as a material that shrinks, which does not return to its original size when exposed to a temperature below the low temperature limit. When the cartridge 141 is exposed to such temperature, the fuse 145 may be affected so as to open up the bypass channel 145. This opening of the bypass channel 145 may cause an error detectable by a cartridge analyzer when the cartridge 141 is inserted into the analyzer.

Figure 15:
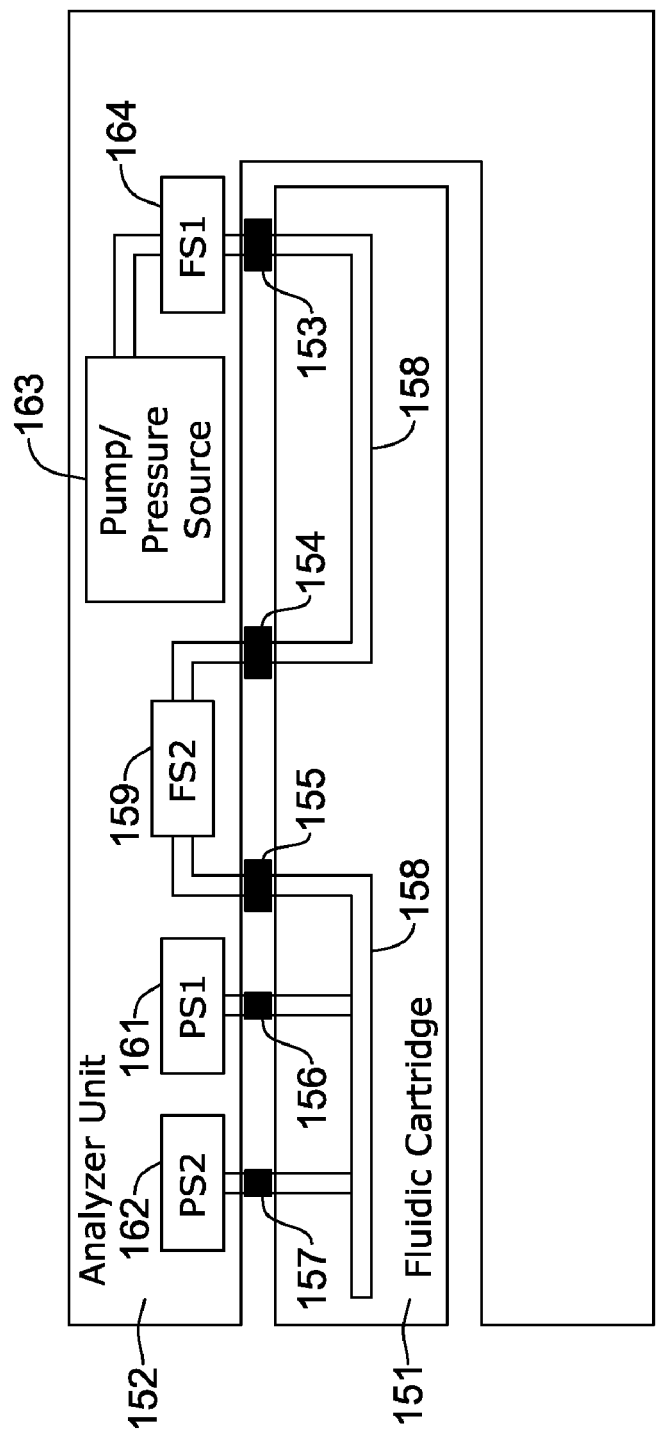
FIG. 15 shows a setup for off-cartridge flow sensing.

FIG. 15 shows an approach for off-cartridge flow sensing. The Figure shows the cartridge 151 connected to a cartridge analyzer unit 152. There may be interfaces 153, 154 and 155 between ports of the cartridge 151 and analyzer unit 152. There may be additional or alternative interfaces 156 and 157 between ports of the cartridge 151 and analyzer unit 152. On-cartridge flow rate detection may use off-cartridge sensors. An on-cartridge flow channel 158 may be routed off-cartridge to an off-cartridge flow sensor 159 via interfaces 154 and 155, respectively, for flow measurements. Alternatively, or in addition, two or more off-cartridge pressure sensors 161 and 162 may be fluidly connected to two points along the on-cartridge flow channel 158 via interfaces, 156 and 157, respectively, to detect the flow rate in the channel 158. Also, an off-cartridge pump/pressure source 163 via an off-cartridge flow sensor 164 and the interface 153 may provide a fluid flow for the on-cartridge flow channel 158.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:
1. A microfluidic analyzer system comprising:
   an analyzer unit;
   a fluidic circuit having an input port in fluid communication with the analyzer unit;
   a first flow sensor positioned within the analyzer unit;
   a second flow sensor positioned within the fluidic circuit and in fluid communication with the first flow sensor;
   a pump/pressure source having an output connected directly to the first flow sensor; and
   a processor connected to the flow sensors and the fluidic circuit; and wherein each of the flow sensors include an upstream temperature sensor, a thermally isolated heater, and a downstream temperature sensor, wherein the upstream and downstream temperature sensors are positioned on either side of the heater;

wherein a fluid flow rate is proportional to the temperature difference between the upstream and downstream temperature sensors; and wherein a first flow rate at the first flow sensor and a second flow rate at the second flow sensor are compared to detect a leak between an interface of the analyzer unit and the fluidic circuit.

2. The system of claim 1, wherein the fluidic circuit may be of a hematology analyzer.

3. The system of claim 1, wherein:
the flow rates at the flow sensors are sent to the processor;
a result at the fluidic circuit is sent to the processor; and
the processor performs result correction in accordance with the flow rates.

4. The system of claim 3, wherein:
the flow rates are volume per time;
the result at the fluidic circuit is a count per time; and
a result from the processor is a count per volume.

5. The system of claim 3, wherein:
the second flow rate is a number of microliters per second;
the result sent to the processor is a number of cells per second; and
a result from the processor is the number of cells per second divided by the number of microliters per second to be a number of cells per microliter.

6. The system of claim 1, wherein:
the processor provides a signal to the pump/pressure source; and
the processor performs closed-loop control of the flow rates, according to the flow sensors, provided by the pump/pressure source.

7. The system of claim 6, wherein:
the flow rates are volume per time;
the result at the fluidic circuit is a count per time; and
a result from the processor is a count per volume.

8. The system of claim 6, wherein:
the flow rates are a number of microliters per second;
the result sent to the processor is a number of cells per second; and
a result from the processor is the number of cells per second divided by the number of microliters per second to be a number of cells per microliter.

9. A microfluidic analyzer system comprising:
a fluidic circuit having an input port;
a flow sensor configured to also function as an instrumentation diagnostics sensor, the flow sensor connected to the input port;
a pump/pressure source having an output connected to the flow sensor;
a processor connected to the flow sensor and the fluidic circuit; and
a temperature sensor in fluid communication with the flow sensor;
a thermal conductivity sensor positioned in-line with the temperature sensor; and
a viscosity sensor positioned in-line with the thermal conductivity sensor; and
wherein the flow sensor includes an upstream temperature sensor, a thermally isolated heater, and a downstream temperature sensor, wherein the upstream and downstream temperature sensors are positioned on either side of the heater; and
wherein the processor adjusts a fluid flow rate in the fluidic circuit according to a temperature difference between the upstream and downstream temperature sensors.

10. The system of claim 9, wherein the microfluidic analyzer is a hematology analyzer and the fluidic circuit is configured for hematology analysis.

11. The system of claim 9, wherein:
a flow rate at the flow sensor is sent to the processor;
a result at the fluidic circuit is sent to the processor; and
the processor performs result correction in accordance with the flow rate.

12. The system of claim 11, wherein:
the flow rate is volume per time;
the result at the fluidic circuit is a count per time; and
a result from the processor is a count per volume.

13. The system of claim 11, wherein:
the flow rate is a number of microliters per second;
the result sent to the processor is a number of cells per second; and
a result from the processor is the number of cells per second divided by the number of microliters per second to be a number of cells per microliter.

14. The system of claim 9, wherein:
the processor provides a signal to the pump/pressure source; and
the processor performs closed-loop control of a flow rate, according to the flow sensor, provided by the pump/pressure source.

15. The system of claim 14, wherein:
the flow rate is volume per time;
the result at the fluidic circuit is a count per time; and
a result from the processor is a count per volume.

16. The system of claim 14, wherein:
the flow rate is a number of microliters per second;
the result sent to the processor is a number of cells per second; and
a result from the processor is the number of cells per second divided by the number of microliters per second to be a number of cells per microliter.

* * * * *